(12) United States Patent
Kiss et al.

(10) Patent No.: US 8,846,027 B2
(45) Date of Patent: Sep. 30, 2014

(54) **COMPOSITIONS FOR THE VAGINAL AND ORAL ADMINISTRATION OF *LACTOBACILLUS* AND USES THEREOF**

(75) Inventors: Herbert Kiss, Vienna (AT); Konrad J. Domig, Vienna (AT); Wolfgang Kneifel, Vienna (AT); Helmut Viernstein, Vienna (AT); Frank M. Unger, Vienna (AT)

(73) Assignee: HSO Health Care GmbH, Vienna (AT)

( * ) Notice: Subject to any disclaimer, the term of this patent is extended or adjusted under 35 U.S.C. 154(b) by 0 days.

(21) Appl. No.: 13/821,431

(22) PCT Filed: Sep. 13, 2011

(86) PCT No.: PCT/EP2011/065877
§ 371 (c)(1),
(2), (4) Date: Mar. 7, 2013

(87) PCT Pub. No.: WO2012/035028
PCT Pub. Date: Mar. 22, 2012

(65) Prior Publication Data
US 2013/0171253 A1 Jul. 4, 2013

Related U.S. Application Data

(60) Provisional application No. 61/412,964, filed on Nov. 12, 2010.

(30) Foreign Application Priority Data

Sep. 14, 2010 (EP) .................................... 10176578

(51) Int. Cl.
*A01N 63/00* (2006.01)
*A01N 65/00* (2009.01)

(52) U.S. Cl.
USPC ........................ 424/93.1; 424/93.4; 424/93.45

(58) Field of Classification Search
None
See application file for complete search history.

(56) References Cited

U.S. PATENT DOCUMENTS

2008/0268006 A1   10/2008   Molin et al.

FOREIGN PATENT DOCUMENTS

WO     2006 038869     4/2006

OTHER PUBLICATIONS

Ehrstrom, S. et al., "Lactic acid bacteria colonization and clinical outcome after probiotic supplementation in conventionally treated bacterial vaginosis and vulvovaginal candidiasis," Elsevier, Microbes and Infection, vol. 12, No. 10, pp. 691 to 699, (Sep. 1, 2010), XP027259939.
Barrons, R. et al., "Use of *Lactobacillus* Probiotics for Bacterial Genitourinary Infections in Women" A Review, Clinical Therapeutics, Excerpta Medica Inc., vol. 30, No. 3, pp. 453 to 468, (Mar. 1, 2008), XP022593705.
Falagas, M. et al., "Probiotics for the treatment of women with bacterial vaginosis," Clinical Microbiology and Infection: The Official Publication of the European Society of Clinical Microbiology and Infectious Diseases, vol. 13, No. 7, pp. 657 to 664, (Jul. 2007), XP002631583.
Czaja, C. et al., "Phase 1 Trial of a *Lactobacillus crispatus* Vaginal Suppository for Prevention of Recurrent Urinary Tract Infection in Women," Infectious Diseases in Obstetrics and Gynecology, vol. 2007, Article ID 35387, Total 8 pages, (Jan. 1, 2007), XP009110731.
Hemmerling, A. et al., "Phase 1 Dose-Ranging Safety Trial of *Lactobacillus crispatus* CTV-05 for the Prevention of Bacterial Vaginosis," Sexually Transmitted Diseases, vol. 36, No. 9, pp. 564 to 569, (Sep. 2009), XP002631584.
Kiss, H. et al., "Vaginal *Lactobacillus microbiota* of healthy women in the late first trimester of pregnancy," BJOG: An International Journal of Obstetrics and Gynaecology, vol. 114, No. 11, pp. 1402 to 1407, (Nov. 2007), XP002631565.
Antonio, M. A. D., et al., "The Identification of Vaginal *Lactobacillus* Species and the Demographic and Microbiologic Characteristics of Women Colonized by These Species," The Journal of Infectious Diseases, vol. 180, No. 6, pp. 1950 to 1956, (Dec. 1, 1999) XP009004729.
International Search Report Issued Nov. 14, 2011 in PCT/EP11/65877 Filed Sep. 13, 2011.

*Primary Examiner* — Albert Navarro
(74) *Attorney, Agent, or Firm* — Oblon, Spivak, McClelland, Maier & Neustadt, L.L.P.

(57) ABSTRACT

The present invention relates to compositions for the oral and vaginal administration of human Lactobacilli and uses thereof for physiologic restoration of the vaginal flora, physiologic maintenance of *Lactobacillus flora* in pathologic deficiency to produce Lactobacilli, treatment of asymptomatic bacterial vaginosis and prevention of preterm delivery caused through bacterial vaginosis.

17 Claims, 6 Drawing Sheets

Fig. 1

| | x | complete inhibition |
|---|---|---|
| | +++ | very strong inhibition |
| | ++ | strong inhibition |
| | + | slight inhibition |
| | - | no inhibition |

| Cd 25, 26 | Candida krusei |
|---|---|
| Cd 30, 31 | Candida albicans |
| Cd 33, 34 | Candida glabrata |
| Ec 5, 6 | Escherichia coli |
| Ga 1, 3 | Gardnerella vaginalis |

| | | after 48 h | | after 120 h | | after 48 h | | after 48 h | | after 48 h | | after 72 h | |
|---|---|---|---|---|---|---|---|---|---|---|---|---|---|
| | | Cd 25 | Cd 26 | Cd 25 | Cd 26 | Cd 30 | Cd 31 | Cd 33 | Cd 34 | Ec 5 | Ec 6 | Ga 1 | Ga 3 |
| Lb. crispatus | LBV 6 | +++ | +++ | x | x | +++ | +++ | + | + | -/+ | + | +++ | +++ |
| | LBV 10 | +++ | ++/+++ | +/++ | - | +++ | ++/+++ | +++ | + | - | -/+ | +++ | +++ |
| | LBV 33 | +++ | +++ | x | x | +++ | +++ | +++ | +++ | -/+ | -/+ | +++ | +++ |
| | LBV 48 | +++ | + | +/++ | - | +++ | ++ | -/+++ | -/+ | -/+ | -/+ | +++ | +++ |
| | LBV 61 | +++ | ++/+++ | ++ | + | +++ | +/++ | +++ | + | - | -/+ | +++ | +++ |
| | LBV 88 | + | - | - | - | +/++ | + | + | + | -/+ | + | +++ | +++ |
| | LBV 92 | +++ | +++ | x | x | +++ | +/+++ | + | + | -/+ | -/+ | +++ | +++ |
| | LBV 100 | +++ | +++ | +++ | +++ | +++ | +++ | + | + | -/+ | -/+ | +++ | +++ |
| Lb. gasseri | LBV 13 | +++ | +++ | ++ | + | +++ | +/++ | + | -/+ | - | + | +++ | +++ |
| | LBV 26 | +++ | +++ | +++ | + | ++ | + | + | + | -/+ | + | +++ | +++ |
| | LBV 28 | + | + | - | - | + | ++ | - | - | - | + | +++ | +++ |
| | LBV 38 | + | + | - | - | ++/+++ | +/++ | - | - | -/+ | - | +++ | +++ |
| | LBV 58 | +++ | +++ | +++ | +++ | +++ | ++ | + | + | -/+ | -/+ | +++ | +++ |
| | LBV 62 | +++ | ++/+++ | +++ | -/+ | +++ | +/++ | + | + | - | -/+ | +++ | +++ |
| | LBV 63 | +++ | +++ | +++ | ++ | ++/+++ | +/++ | + | + | - | - | +++ | +++ |
| | LBV 65 | ++ | + | + | -/+ | ++/+++ | + | + | + | + | + | +++ | +++ |
| | LBV 121 | - | - | +++ | +++ | - | -/+ | - | - | - | - | +++ | +++ |
| | LBV 133 | +++ | +++ | +++ | ++ | + | + | + | + | - | - | +++ | +++ |
| | LBV 146 | + | + | + | -/+ | ++ | ++ | + | + | - | -/+ | +++ | +++ |
| | LBV 149 | +++ | +++ | +++ | +++ | +++ | ++ | + | + | - | -/+ | +++ | +++ |
| | LBV 150 | +++ | +++ | +++ | +++ | +++ | ++ | + | + | -/+ | - | +++ | +++ |
| | LBV 151 | +++ | ++ | + | -/+ | +++ | +/++ | + | + | - | -/+ | +++ | +++ |
| | LBV 152 | +++ | +++ | +++ | +++ | +++ | ++ | + | + | -/+ | -/+ | +++ | +++ |
| | LBV 162 | +++ | +++ | +++ | +++ | +++ | ++ | + | + | - | -/+ | +++ | +++ |
| | LBV 165 | +++ | +++ | ++ | + | ++ | +/++ | + | + | - | -/+ | +++ | +++ |
| | LBV 166 | + | - | - | - | ++ | + | -/+ | -/+ | - | -/+ | +++ | +++ |

Fig. 1 (continued)

| | | after 48 h | | after 120 h | | after 48 h | | after 48 h | | after 48 h | | after 72 h | |
|---|---|---|---|---|---|---|---|---|---|---|---|---|---|
| | | Cd 25 | Cd 26 | Cd 25 | Cd 26 | Cd 30 | Cd 31 | Cd 33 | Cd 34 | Ec 5 | Ec 6 | Ga 1 | Ga 3 |
| Lb. jensenii | LBV 2 | +++ | +++ | ++ | ++ | +++ | ++ | + | + | -/+ | -/+ | +++ | +++ |
| | LBV 3 | ++/+++ | + | - | - | ++ | + | -/+ | -/+ | - | - | +++ | +++ |
| | LBV 8 | x | x | +++ | +++ | +++ | +/++ | + | + | -/+ | -/+ | +++ | +++ |
| | LBV 110 | x | x | +++ | +++ | +++ | +++ | + | + | -/+ | -/+ | +++ | +++ |
| | LBV 111 | ++ | +++ | x | + | ++ | ++ | + | + | -/+ | -/+ | +++ | +++ |
| | LBV 116 | +/++ | -/+ | - | - | ++ | +/++ | + | + | - | + | +++ | +++ |
| Lb. rhamnosus | LBV 69 | +++ | +++ | +++ | +++ | +++ | +++ | +/++ | +/++ | -/+ | + | +++ | +++ |
| | LBV 81 | x | x | x | x | +++ | +++ | + | + | -/+ | -/+ | +++ | +++ |
| | LBV 96 | +++ | +++ | x | +++ | +++ | +++ | ++ | + | -/+ | -/+ | +++ | +++ |
| | LBV 106 | +++ | x | x | x | +++ | +++ | +/++ | +/++ | -/+ | -/+ | +++ | +++ |
| | LBV 136 | x | x | x | x | +++ | +++ | + | + | -/+ | + | +++ | +++ |
| | LBV 143 | x | x | x | x | +++ | +++ | + | + | -/+ | -/+ | +++ | +++ |
| | LBV 147 | +++ | +++ | +++ | +++ | +++ | +++ | +/++ | +/++ | -/+ | -/+ | +++ | +++ |
| | LBV 153 | x | x | x | x | +++ | ++ | + | + | -/+ | -/+ | +++ | +++ |
| | LBV 161 | x | x | x | x | +++ | + | - | - | -/+ | + | +++ | +++ |
| competing products | LB 262 | x | x | +++ | +++ | +++ | +++ | ++ | + | + | + | +++ | +++ |
| | LB 263 | x | +++ | +++ | +++ | +++ | +++ | ++ | ++ | + | + | +++ | +++ |
| | LB 264 | x | x | x | +++ | ++/+++ | ++ | + | + | + | + | +++ | +++ |
| | LB 265 | +++ | + | +++ | +++ | +++ | + | + | - | ++ | + | +++ | +++ |
| | LB 266 | + | + | - | - | +++ | | - | | | | +++ | +++ |

COMPOSITIONS FOR THE VAGINAL AND ORAL ADMINISTRATION OF *LACTOBACILLUS* AND USES THEREOF

CROSS-REFERENCE TO RELATED APPLICATIONS

This application is a National Stage of PCT/EP2011/065877 filed on Sep. 13, 2011. This application is based upon and claims the benefit of priority to European Application No. 10176578.2 filed on Sep. 14, 2010. This application is based upon and claims the benefit of priority to U.S. Provisional Application No. 61/412,964 filed on Nov. 12, 2010.

The present invention relates to compositions for the oral and vaginal administration of human Lactobacilli and uses thereof for physiologic restoration of the vaginal flora, physiologic maintenance of *Lactobacillus flora* in pathologic deficiency to produce Lactobacilli, treatment of asymptomatic bacterial vaginosis and prevention of preterm delivery caused through bacterial vaginosis.

The healthy human vagina is dominated by a variety of *Lactobacillus* species, which play an essential role in protecting women from urogenital infection. Lactobacilli have the ability to adhere to vaginal epithelia, to inhibit the adhesion and growth of pathogens, deplete nutrients otherwise available to pathogens, and modulate the host immune response and microenvironment [1,2]. Most importantly, Lactobacilli metabolize the glycogen contained in the cells of the vaginal vault, forming lactic acid as the final product. Thus, in a healthy vagina, pH-values of 4.0-4.5 are reached, a level at which many pathogens cannot flourish.

Because vaginal infection is an important mechanism of disease responsible for preterm birth [3], maintaining the natural, healthy balance of the *Lactobacillus flora* in the vagina is particularly important during pregnancy. A deficiency in Lactobacilli can upset the microbial balance in the vagina, frequently resulting in the syndrome of bacterial vaginosis [4,5], which may be associated with a quantitative and qualitative shift from normally occurring Lactobacilli to a mixed flora dominated by anaerobic bacteria [6]. According to Nugent et al. [7], bacterial vaginosis is characterized by a complete loss of Lactobacilli and a concomitant increase in Gram-variable and Gram-negative rods, primary among them *Gardnerella vaginalis* as well as *Bacteroides, Prevotella*, and *Mobiluncus* species [4,5]. However, loss of vaginal Lactobacilli also leaves nonpregnant women susceptible to infection which may result in endometritis or even pelvic inflammatory disease [8, 9].

During menopause, involution of the female genital tract occurs, reflecting possibly a built-in biologic life expectancy interrelated with the neurohypophyseal endocrine axis [10]. The major universal change is vaginal atrophy [10]. Vaginal dryness, burning, itching and dyspareunia are frequent complaints along with dysuria, urinary frequency and recurrent infections. The genitourinary atrophy following menopause is associated with a decline in estrogen secretion accompanied by depletion of Lactobacilli and increased colonization by pathogenic microorganisms associated with bacterial vaginosis and urinary tract infections [11]. In post-menopausal women, vaginal estriol therapy reduces *E. coli* colonization and increases the numbers of Lactobacilli, with the result that the incidence of recurrent urinary and genital tract infections drops significantly [12].

Several species of *Lactobacillus* have been described to populate the vagina to varying degrees. For some time the flora of healthy women of childbearing age was believed to be dominated by *Lactobacillus acidophilus* and *Lactobacillus fermentum*, followed by *Lactobacillus brevis, Lactobacillus jensenii* and *Lactobacillus casei* [13]. In their study on the vaginal *Lactobacillus flora* [14], Vásquez et al. found that the vaginal flora of most participants was dominated by a single *Lactobacillus* species, with the presence of other species showing wide individual variability. The most frequently occurring species were *L. crispatus, L. gasseri, L. iners*, and *L. jensenii*. In another study by Reid et al., the most commonly isolated *Lactobacillus* strains were *L. jensenii, L. acidophilus, L. casei*, and *L. gasseri* [15]. In recent Austrian studies, the predominant *Lactobacillus* species identified by species-specific PCR, namely *L. crispatus, L. gasseri, L. jensenii*, and *L. rhamnosus* were used to generate DNA fingerprints. *L. crispatus, L. gasseri, L. jensenii* and *L. rhamnosus* can be regarded as the predominant species in the vagina [16].

To remedy deficiencies in the *Lactobacillus flora* (and hence, in the protective capability of the vaginal flora), the administration of vaginal suppositories containing Lactobacilli is the most common way of Lactobacilli substitution. Some authors believe that the topical use of Lactobacilli is a safe and promising treatment for the prevention of vaginosis and recurrent urinary tract infections [17].

While vaginal supplementation is a long-standing, widely accepted practice for Lactobacilli substitution, oral administration of a *Lactobacillus* preparation represents a new concept for the restitution of a normal vaginal flora. Recent results indicate that the probiotic strains *L. rhamnosus* GR-1 (ATCC 55826) and *L. reuteri* RC-14 (ATCC 55845) can be taken orally on a daily basis for two months without any side effects [18]. The consumption then resulted in a significant improvement of the vaginal flora in terms of increased Lactobacilli presence and decreased yeast and coliforms. While one group of authors discussed the beneficial effects in terms of an alteration in mucosal immunity or of probiotic bacteria ascending to the vagina from the rectal area [18], another group recently demonstrated, by species-specific PCR-amplification, that *L. rhamnosus* GR-1 and *L. reuteri* RC-14 can be delivered to the vaginal environment when administered orally [19].

These preliminary findings were substantiated in a randomized, double-blind, placebo controlled study of oral Lactobacilli to improve the vaginal flora of postmenopausal women. Postmenopausal women with Nugent score between 4 and 6 (indicative of an intermediate floral quality) in initial vaginal swab were randomized in two groups. Women in the intervention group received probiotic capsules containing $2.5 \times 10^9$ cfu (colony forming units) each of lyophilized *L. rhamnosus* GR-1 and *L. reuteri* RC-14 and women in the control group received an oral placebo once daily, in both groups for 14 days. Final vaginal swabs were taken one day after the last administration of the probiotic. Twenty-one of the 35 subjects (60%) in the intervention group and 6 of the 37 subjects (16%) in the control group showed a reduction in the Nugent score by at least 2 grades (p=0.001). The median difference in Nugent score between baseline and the end of the study was 3 in the intervention and 0 in the control group (p=0.0001)[20].

Whereas *L. rhamnosus* GR-1 and *L. reuteri* RC-14 clearly shifted the quality of the vaginal flora from intermediate to normal in 60% of women of an intervention group, one patient in the intervention group who had a Nugent score of 8 (indicative of bacterial vaginosis) at inclusion, failed to improve despite oral *Lactobacillus*. This might indicate that administration of Lactobacilli alone lacks therapeutic efficacy in cases of bacterial vaginosis. Indeed, therapeutic studies aimed at curing bacterial vaginosis have used the probiotic combination *L. rhamnosus* GR-1 and *L. reuteri* RC-14 as adjunct to Metronidazole or Tinidazole chemotherapy. Thus, in a randomized double-blind, placebo controlled trial, 125 premenopausal women were enrolled who had been diagnosed with bacterial vaginosis. The subjects were treated with oral Metronidazole (500 mg) twice daily from days one to seven and randomized to receive oral L. rhamnosus GR-1 and L. reuteri RC-14 ($1 \times 10^9$ cfu each) or a placebo twice daily from day one to 30. Primary outcome was cure of bacterial vaginosis (no symptoms or sign of vaginosis) at day 30. A total of 106 subjects returned for 30 day follow up of which 88% were cured in the antibiotic—probiotic group compared to 40% in the antibiotic placebo group (p<0.001). Of the remaining subjects, 30% in the placebo group and none in the probiotic group had bacterial vaginosis, while 30% in the placebo and 12% in the probiotic group fell into the intermediate category. In summary, the study showed efficacious use of Lactobacilli and antibiotic in the eradication of bacterial vaginosis in African women [21]. In a similar study performed in Brazil, 64 women diagnosed with bacterial vaginosis were randomly assigned to receive a single dose of Tinidazole (2 g) supplemented with either 2 placebo capsules or two capsules containing L. rhamnosus GR-1 and L. reuteri RC-14 every morning for the following four weeks. At the end of treatment the probiotic group had a significantly higher cure rate of bacterial vaginosis (87.5%) than the placebo group (50%) (p=0.001). In addition, according to the Nugent score, more women were assessed with "normal" vaginal microbiota in the probiotic group (75% vs. 34.4% in the placebo group; p=0.011). This study showed that probiotic Lactobacillus can provide benefits to women being treated with antibiotics for an infectious condition [22]. Together the results of clinical studies indicate that in cases of bacterial vaginosis improvement of Nugent scores with probiotics alone, without administration of an antibiotic or chemotherapeutic can not be achieved with the preparations available in the prior art.

The author of the present invention has now found a new probiotic composition, comprising at least four Lactobacillus strains of human origin and capable of improving the vaginal flora.

It has now been surprisingly found, that in a controlled trial, oral administration over only two weeks of a combination of Lactobacillus crispatus, Lactobacillus rhamnosus, Lactobacillus jensenii and Lactobacillus gasseri, contrary to the prior art in the absence of antibiotic, the Nugent scores of the participants were lowered from an average of 8 (indicative of bacterial vaginosis) to an average of 6 (indicative of an intermediate floral quality).

In addition, the strains of the invention showed significant production of extracellular hydrogen peroxide. As hydrogen peroxide serves to kill noxious microorganisms, this is an important advantage for the composition of Lactobacilli strains of the invention. Therefore, an object of the present invention is a dietetic or pharmaceutical composition based on microbial cultures, preferably lyophilized cultures or liquid cultures such as yogurt and other fermented and/or non fermented drinks, comprising at least four Lactobacillus strains autochthonous with respect to human, said strains being selected from the group consisting of Lactobacillus crispatus LBV 88 (DSM 22566), Lactobacillus rhamnosus LBV 96 (DSM 22560), Lactobacillus jensenii LBV 116 (DSM 22567), Lactobacillus gasseri LBV 150N (DSM 22583), Lactobacillus crispatus LBV 10 (DSM 23744), Lactobacillus crispatus LBV 61 (DSM 23745), Lactobacillus jensenii LBV 8 (DSM 23746) Lactobacillus jensenii LBV 110 (DSM 23747), Lactobacillus rhamnosus LBV 69 (DSM 23748), Lactobacillus rhamnosus LBV 136 (DSM 23749), Lactobacillus gasseri LBV 162 (DSM 23750) and Lactobacillus gasseri LBV 62 (DSM 23751), together with pharmaceutically or nutritionally acceptable carriers, adjuvants and/or excipients.

The twelve strains above cited have been submitted to DSMZ for patent deposit (Deutsche Sammlung von Mikroorganismen and Zellkulturen GmbH, German Collection of Microorganisms and Cell Cultures located at Inhoffenstr. 7 B, D-38124 Braunschweig, Germany). The strains Lactobacillus crispatus LBV 88 (DSM 22566), Lactobacillus rhamnosus LBV 96 (DSM 22560), Lactobacillus jensenii LBV 116 (DSM 22567), and Lactobacillus gasseri LBV 150N (DSM 22583) were originally deposited on Apr. 1, 2009, and were granted the accession numbers DSM 22566, DSM 22560, and DSM 22567 on May 7, 2009, and DSM 22583 on May 19, 2009. The strains Lactobacillus crispatus (DSM 23744), Lactobacillus crispatus (DSM 23745), Lactobacillus jensenii (DSM 23746) Lactobacillus jensenii (DSM 23747), Lactobacillus rhamnosus (DSM 23748), Lactobacillus rhamnosus (DSM 23749), Lactobacillus gasseri (DSM 23750), and Lactobacillus gasseri (DSM 23751) were deposited and granted the accession numbers DSM 23744, DSM 23745, DSM 23746, DSM 23747, DSM 23748, DSM 23749, DSM 23750, and DSM 23751 on Jul. 6, 2010.

The compositions according to the present invention may comprise additional nutritional components including but not limited to at least one of the following components: vitamins, antioxidants such as preparations from pomegrenade or soybean flavonoids, fibers (inulin and fructooligosaccharides), mineral salts, phytoderivatives, milk (fermented or non-fermented milk, including yogurt).

The preparation of the invention comprises Lactobacilli of human origin. These Lactobacilli represent a physiologic composition.

Each of the aforementioned Lactobacillus species is present in a concentration ranging from $0.05 \times 10^9$ CFU/g to $30 \times 10^9$ CFU/g, preferably from $0.5 \times 10^9$ CFU/g to $25 \times 10^9$ CFU/g.

According to a preferred embodiment of the present invention, the composition comprises a combination of Lactobacillus strains consisting of Lactobacillus crispatus (DSM 22566), Lactobacillus rhamnosus (DSM 22560), Lactobacillus jensenii (DSM 22567) and Lactobacillus gasseri (DSM 22583). In such preferred composition of the invention, Lactobacillus crispatus (DSM 22566) is present in a range of concentration comprised between $3 \times 10^9$ and $22 \times 10^9$ CFU/g, Lactobacillus rhamnosus (DSM 22560) is present in a range of concentration comprised between $3 \times 10^9$ and $22 \times 10^9$ CFU/g, Lactobacillus jensenii (DSM 22567) is present in a range of concentration comprised between $0.7 \times 10^9$ and $6 \times 10^9$ CFU/g, Lactobacillus gasseri (DSM 22583) is present in a range of concentration comprised between $1 \times 10^9$ and $8 \times 10^9$ CFU/g.

In a more preferred embodiment of the invention, the composition of the present invention comprises Lactobacillus crispatus (DSM 22566) in a concentration of $6 \times 10^9$ CFU/g, Lactobacillus rhamnosus (DSM 22560) in a concentration of $6 \times 10^9$ CFU/g, Lactobacillus jensenii (DSM 22567) in a concentration of $1.2 \times 10^9$ CFU/g and Lactobacillus gasseri (DSM 22583) in a concentration of $1.8 \times 10^9$ CFU/g.

In another more preferred embodiment of the invention, the composition of the present invention comprises Lactobacillus crispatus (DSM 22566) in a concentration of $20 \times 10^9$ CFU/g, Lactobacillus rhamnosus (DSM 22560) in a concentration of $20 \times 10^9$ CFU/g, Lactobacillus jensenii (DSM 22567) in a concentration of $4 \times 10^9$ CFU/g and Lactobacillus gasseri (DSM 22583) in a concentration of $6 \times 10^9$ CFU/g.

According to a preferred embodiment, the dietetic or pharmaceutical composition of the present invention has the composition described in Tables 1 or in Table 2.

TABLE 1

| Composition 1 | Quantity (mg/dose) | Guaranteed viable cell count (CFU/dose) | Initial viable cell count (CFU/dose) |
|---|---|---|---|
| L. crispatus Lbv88 (DSM 22566) | 15 | $1 \times 10^9$ | $1.5 \times 10^9$ |
| L. rhamnosus LbV96 (DSM 22560) | 15 | $1 \times 10^9$ | $1.5 \times 10^9$ |
| L. jensenii LbV 116 (DSM 22567) | 20 | $0.2 \times 10^9$ | $0.3 \times 10^9$ |
| L. gasseri LbV 150N (DSM 22583) | 9 | $0.3 \times 10^9$ | $0.45 \times 10^9$ |
| Potato maltodextrin | 161 | | |
| Insoluble dietary fiber | 25 | | |
| Silicium dioxide | 5 | | |
| Total | 250 | | |

TABLE 2

| Composition 2 | Quantity (mg/dose) | Guaranteed viable cell count (CFU/dose) | Initial viable cell count (CFU/dose) |
|---|---|---|---|
| L. crispatus Lbv88 (DSM 22566) | 50 | $1 \times 10^9$ | $5 \times 10^9$ |
| L. rhamnosus LbV96 (DSM 22560) | 50 | $1 \times 10^9$ | $5 \times 10^9$ |
| L. jensenii LbV 116 (DSM 22567) | 67 | $0.2 \times 10^9$ | $1 \times 10^9$ |
| L. gasseri LbV 150N (DSM 22583) | 30 | $0.3 \times 10^9$ | $1.5 \times 10^9$ |
| Potato maltodextrin | 23 | | |
| Insoluble dietary fibre | 25 | | |
| Silicium dioxide | 5 | | |
| Total | 250 | | |

Application forms of the compositions according to the inventions suitable for oral intake or topical vaginal administration are preferred. As an example, probiotic bacteria for female use can be administered orally in the form of capsules, or (filled in sachets) suspended in a drink, or in the form of fermented milk (yogurt). When administered orally, they are expected to survive passage through the stomach and duodenum (displaying a certain stability towards acid and bile) and temporarily colonize the gut. From there, small numbers of bacteria will ascend to the vagina and (again temporarily) colonize the vaginal mucosa. Probiotic bacteria can also be used conventionally as vaginal capsules or suppositories and directly applied to the vagina. The protective effect of Lactobacilli against potential pathogens in the vagina is generated through the metabolic activity of the Lactobacilli. The bacteria consume glycogen and other sources of glucose and produce lactic acid. The low pH generated in this manner is harmful to the less desirable bacteria and fungi and thus protects the vaginal mucosa against infections. Therefore, pharmaceutical compositions according to the invention may be administered in the form of suppositories, vaginal capsules for vaginal administration or as coated capsules, tablets, sachets, pills, pearls, vials for oral intake as well as yogurt, yogurt drinks, fermented milk, juices, and other fermented drinks and foods.

The present invention further relates to dietetic or pharmaceutical compositions based on microbial cultures of Lactobacilli, preferably lyophilized cultures or liquid cultures such as yogurt and other fermented and/or non fermented drinks, comprising at least four Lactobacillus strains, autochthonous with respect to human, selected from the group consisting of Lactobacillus crispatus (DSM 22566), Lactobacillus rhamnosus (DSM 22560), Lactobacillus jensenii (DSM 22567), Lactobacillus gasseri (DSM 22583), Lactobacillus crispatus (DSM 23744), Lactobacillus crispatus (DSM 23745), Lactobacillus jensenii (DSM 23746) Lactobacillus jensenii (DSM 23747), Lactobacillus rhamnosus (DSM 23748), Lactobacillus rhamnosus (DSM 23749), Lactobacillus gasseri (DSM 23750) and Lactobacillus gasseri (DSM 23751), for use in the treatment of vaginal and female urogenital infections caused by Lactobacillus deficiency, preferably selected between vaginosis or vaginitis, chronic bacterial vaginosis and chronic yeast infection, chronic urinary tract infection in menopause, atrophic vaginitis or vaginosis and similar infections as abacterial vaginosis. In fact, these Lactobacilli are for oral or vaginal administration for physiologic restoration of the vaginal flora and for a physiologic maintenance of a Lactobacillus flora in pathologic deficiency to produce Lactobacilli.

In addition, the compositions according to the invention are particularly suitable for use in the treatment or prevention of asymptomatic and recurrent bacterial vaginosis in pregnancy or preterm delivery caused by bacterial vaginosis.

Further embodiments of the present invention are represented by integrators, dairy products, drinks and/or food products for human nutrition characterized in that they contain a dietetic composition as above defined.

Dairy products of the present invention can consist of milk, yogurt, cheese, homogenized products (based on milk, cheese, fruit), fermented or non-fermented milk (including powdered milk, non-lactose containing milk, milk shakes) containing probiotics. Therapeutic cheese can be obtained by the addition of suitable probiotic microorganisms in a concentrated dried form in a certain processing phase of the cheese in order to guarantee the supply of the dose of the microorganisms necessary for the organism. The drinks can be instantaneous drinks or water containing the compositions according to the present invention.

Said integrators, dairy and food products are particularly suitable for use in the treatment or prevention of asymptomatic or recurrent bacterial vaginosis, vulvo-vaginal candidosis, preterm delivery caused by bacterial vaginosis or recurrent urinary tract infections.

Finally, the invention is directed to a combination of four probiotic strains autochthonous with respect to human consisting of Lactobacillus crispatus (DSM 22566), Lactobacillus rhamnosus (DSM 22560), Lactobacillus jensenii (DSM 22567) and Lactobacillus gasseri (DSM 22583) for medical use in the treatment of affections of the urogenital tract of women.

The present invention is now described for illustrative but non-limiting purposes, according to its preferred embodiments in the following examples and enclosed Figure wherein:

FIG. 1 illustrates a Table with the results of the antimicrobial effect of the 12 selected strains according to the invention against the five competitor strains of different pathogens, like Candida krusei, Candida albicans, Candida glabrata, Escherichia coli, Gardnerella vaginalis.

EXAMPLES

Example 1

Figure 2:
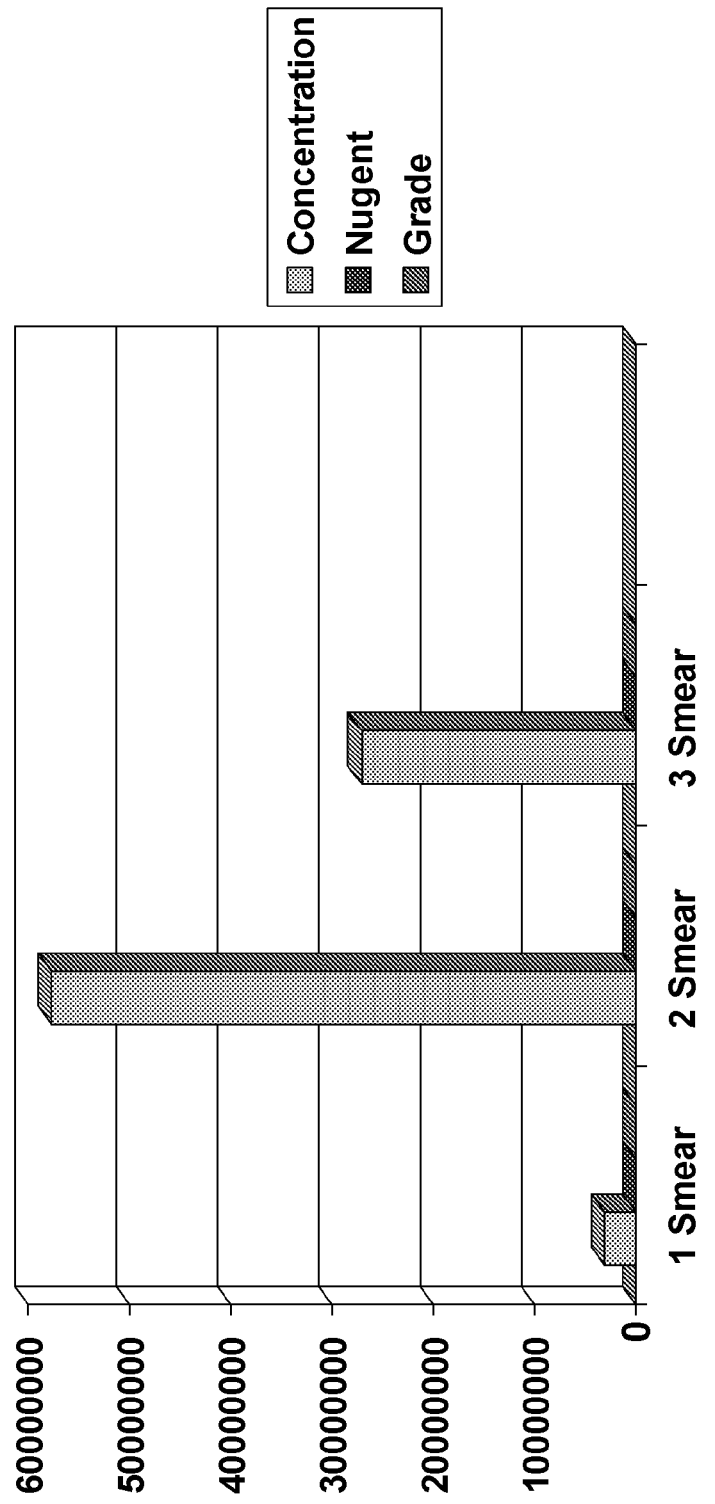
FIGS. 2 and 3 depicts the overall median concentration of Lactobacilli delivered in the vagina in the clinical study of Example 3.

Formulation of the Probiotic Compositions According to the Invention

Patent Deposit of the Twelve Strains Chosen

The twelve preferred strains chosen have been submitted to DSMZ for patent deposit (Deutsche Sammlung von Mikroorganismen and Zellkulturen GmbH, German Collection of Microorganisms and Cell Cultures). They have been selected from an initial sample of 168 colonies isolated from 84 women. An initial selection process led to 41 strains considered candidates for inclusion in a commercial product (9 strains of *L. rhamnosus*, 6 strains of *L. jensenii*, 8 strains of *L. crispatus* and 18 strains of *L. gasseri*). In a second selection step, 12 strains were selected, as follows: *Lactobacillus crispatus* (DSM 22566), *Lactobacillus rhamnosus* (DSM 22560), *Lactobacillus jensenii* (DSM 22567) and *Lactobacillus gasseri* (DSM 22583), *Lactobacillus crispatus* (DSM 23744), *Lactobacillus crispatus* (DSM 23745), *Lactobacillus jensenii* (DSM 23746) *Lactobacillus jensenii* (DSM 23747), *Lactobacillus rhamnosus* (DSM 23748), *Lactobacillus rhamnosus* (DSM 23749), *Lactobacillus gasseri* (DSM 23750), *Lactobacillus gasseri* (DSM 23751), together with pharmaceutically or nutritionally acceptable adjuvants and/or excipients.

The sample cultures transmitted by DSMZ for back-checking have been re-typed and found in agreement with the initially transmitted cultures.

Preparation of the Capsules Product

The compositions according to the invention will be administered in capsule form.

The first step consists in the preparation of the lyophilized cultures of the probiotic strains intended to be used (in a preferred embodiment of the invention, the four strains *Lactobacillus rhamnosus* LBV 96 (DSM 22560), *Lactobacillus crispatus* (DSM 22566), *Lactobacillus jensenii* (DSM 22567) and *Lactobacillus gasseri* (DSM 22583)).

The common steps followed in the manufacture of the lyophilized culture are: activation of the strain (laboratory sub-cultivations), industrial fermentation, separation of the bacterial biomass, generally by centrifugation or nanofiltration, washing of the biomass, cryoprotection of the biomass, freeze-drying, grinding of the "cake" and standardization of the number of viable cells per gram.

After the manufacture of the strains, a pilot or industrial mixing of probiotics with the other excipients to be used follows (if necessary, proper pre-mixes of minority components could be performed).

After the manufacture of this final blend, the capsules are filled with a proper laboratory or industrial capsule filler. The machine could be manual, semi-automatic or completely automatic. Such process is well-known to a person skilled in the art.

Preferred Formulation

The active formulation used in the clinical study, i.e. the composition 1, is depicted in the following Table 3:

TABLE 3

| Composition 1 | Quantity (mg/dose) | Guaranteed viable cell count (CFU/dose) | Initial viable cell count (CFU/dose) |
|---|---|---|---|
| *L. crispatus* Lbv88 (DSM 22566) | 15 | $1 \times 10^9$ | $1.5 \times 10^9$ |
| *L. rhamnosus* LbV96 (DSM 22560) | 15 | $1 \times 10^9$ | $1.5 \times 10^9$ |
| *L. jensenii* LbV 116 (DSM 22567) | 20 | $0.2 \times 10^9$ | $0.3 \times 10^9$ |
| *L. gasseri* LbV 150N (DSM 22583) | 9 | $0.3 \times 10^9$ | $0.45 \times 10^9$ |
| Potato maltodextrin | 161 | | |
| Insoluble dietary fiber | 25 | | |
| Silicium dioxide | 5 | | |
| Total | 250 | | |

The corresponding product formulation (considering a 5 times overdosage), i.e. composition 2, is detailed in the following Table 4:

TABLE 4

| Composition 2 | Quantity (mg/dose) | Guaranteed viable cell count (CFU/dose) | Initial viable cell count (CFU/dose) |
|---|---|---|---|
| *L. crispatus* Lbv88 (DSM 22566) | 50 | $1 \times 10^9$ | $5 \times 10^9$ |
| *L. rhamnosus* LbV96 (DSM 22560) | 50 | $1 \times 10^9$ | $5 \times 10^9$ |
| *L. jensenii* LbV 116 (DSM 22567) | 67 | $0.2 \times 10^9$ | $1 \times 10^9$ |
| *L. gasseri* LbV 150N (DSM 22583) | 30 | $0.3 \times 10^9$ | $1.5 \times 10^9$ |
| Potato maltodextrin | 23 | | |
| Insoluble dietary fibre | 25 | | |
| Silicium dioxide | 5 | | |
| Total | 250 | | |

Preparation Of Probiotic Enriched Fresh Milk for Human Use

A stability assessment of the four strains *Lactobacillus jensenii* LbV 116 (DSM 22567), *Lactobacillus rhamnosus* LbV 96 (DSM 22560), *Lactobacillus gasseri* LbV 150N (DSM 22583) and *Lactobacillus crispatus* LbV 88 (DSM 22566) in standard, pasteurized fresh milk has been made.

The daily dose of milk has been considered as 167 ml (approximately the content of a glass). The aim is to guarantee 2.5 billion of viable cells at the end of shelf-life. The formulation proposal has been defined according to the product which is currently being clinically tested at University Hospital of Vienna. The overage considered for our first evaluation was 5 times.

In the following Table 5 the detailed formulation is shown:

TABLE 5

| Composition 3 | Dose recipe mg/ml | Liter recipe mg/ml | Initial viable cell count/dose | Declared viable cell count/dose |
|---|---|---|---|---|
| *Lactobacillus jensenii* LbV 116 (DSM 22567) | 20 | 119.76 | 1 billion | 0.2 billion |
| *Lactobacillus rhamnosus* | 50 | 299.4 | 5 | 1 |

TABLE 5-continued

| Composition 3 | Dose recipe mg/ml | Liter recipe mg/ml | Initial viable cell count/dose | Declared viable cell count/dose |
|---|---|---|---|---|
| LbV 96 (DSM 22560) Lactobacillus gasseri LbV LbV150N(DSM 22583) | 30 | 179.64 | billion 1.5 billion | billion 0.3 billion |
| Lactobacillus crispatus LbV 88 (DSM 22566) | 50 | 299.4 | 5 billion | 1 billion |
| Total (powder) | 150 | 898.2 | | |
| Fresh pasteurized milk | 167 | 1.000 | | |

In the following Table 6 preliminary stability data of the four strains in milk stored at 4° C. are reported:

TABLE 6

| | | | Stability at 4° C. | | | | |
|---|---|---|---|---|---|---|---|
| | | | 6 days | | | 15 days | |
| Sample | T zero viable cell count ($10^9$ UFC/dose) | pH | Viable cell count ($10^9$ UFC/dose) | pH | Half life (days) | Viable cell count ($10^9$ UFC/dose) | pH | Half life (days) |
| Probiotics in fresh milk | 12.9 | 6.69 | 11.8 | 6.68 | 46.7 | 11.4 | 6.65 | 84.1 |

The mean shelf-life of an industrial, pasteurized fresh milk is 6 days. In any case, we decided to assess stability up to 15 days in order to gain a more complete overview of the behavior of bacterial cells in milk.

As can be inferred from the above data, the probiotics of the invention are very stable in fresh industrial milk. The data suggest that the project is feasible with only a little overage at manufacturing time.

Another aspect to be considered is that pH remained substantially unchanged even after 15 days storage at 4° C. This means that probiotics are not metabolically active in these conditions, which is a certainly desirable aspect.

Example 2

Comparative Study Between the Probiotic Microorganisms According to the Invention and Commercial Products A. Molecular Comparison with Selected Competitor Strains Molecular typing of the selected strains in comparison with a range of competitor strains was performed according to several methods (RAPD-PCR, GTG5 REP-PCR, PFGE).

The following competitor strains available on the market were examined.

Lactobacillus rhamnosus GR-1 (ATCC 55826) (Ombé® product—see EP1137423)
Lactobacillus reuteri RC-14 (ATCC 55845) (Ombé® product—see EP1137423)
Lactobacillus casei rhamnosus (Gynophilus®)
Lactobacillus acidophilus (Gynoflor®)
Lactobacillus gasseri (Döderlein Med®)
Lactobacillus LN 40 (Ellen®)
Lactobacillus fermentum LN 99 (Ellen®)
Lactobacillus casei LN 133-2 (Ellen®)

The selected strains were distinguishable from all competitor strains examined by RAPD-PCR and Primer 4. PFGE following restriction with ApaI or SmaI also showed differences between the strains examined (data not shown).

B. Testing of the Antimicrobial Properties Against Selected Pathogens In Vitro

Tests to explain the antimicrobial mechanism of action were carried out using two strains per target species (Lactobacillus crispatus: LBV 10 (DSM 23744), LBV 88 (DSM 22566); Lactobacillus gasseri: LBV 162 (DSM 23750), LBV 150N (DSM 22583); Lactobacillus jensenii: LBV 110 (DSM23747), LBV 8 (DSM 23746); Lactobacillus rhamnosus: LBV 69 (DSM 23748), LBV 96 (DSM 22560)) on three pathogenic vaginal strains (Gardnerella vaginalis Ga 3, Candida albicans Cd 30 and Candida glabrata Cd 34—see Table 5) using a smear-spotting method.

Here the antimicrobial effect of the live active Lactobacilli strains was tested against live active pathogenic strains. Parallel smears of the Lactobacilli strains are first placed on an agar plate at a separation of about 2 cm. When antimicrobial substances are formed and released by the Lactobacilli strains, these diffuse into the growth medium and form an antimicrobial inhibitory strip into which the live pathogenic strains are spotted. At the same time spotting of the same pathogenic strains is carried out outside the parallel smear as a growth control. No growth or poor growth of the pathogenic strains within the smear compared to the growth control outside the smear indicates the formation of antimicrobial substances by the Lactobacilli being tested [23]. A requirement for the smear-spotting method is a method of cultivation in which both the Lactobacilli and the pathogenic strains demonstrate good growth, which proved to be a problem mainly in the cultivation of Gardnerella vaginalis. In the course of the tests several methods of cultivating Gardnerella vaginalis were tested where neutralised MRS starch agar (pH 6.7, 1% starch) proved to be the best growth medium.

TABLE 7

| Designation of the pathogenic strains | |
|---|---|
| Designation | Species |
| Ec 5 | Escherichia Coli LMG 9007 |
| Ec 6 | Escherichia Coli LMG 10266 |
| Ga 1 | Gardnerella vaginalis LMG 7832 |
| Ga 3 | Gardnerella vaginalis LMG 14325 |
| Cd 25 | Candida krusei |
| Cd 26 | Candida krusei |
| Cd 30 | Candida albicans IHEM 9863 |
| Cd 31 | Candida albicans IHEM 3243 |
| Cd 33 | Candida glabrata IHEM 4210 |
| Cd 34 | Candida glabrata IHEM 19237 |

Experimental Setup

Parallel smears of Lactobacilli strains on an agar plate at a separation of about 2 cm (using various growing media depending on the pathogenic strains being tested: see Table 8).

Incubation of the smears at 37° C., 24 h, anaerobically.

Spotting 5 µl of the active pathogenic strains between the parallel smears and as a growth control outside the smears and subsequent incubation (different conditions depending on the pathogenic strains being tested: see Table 8).

Evaluation of the growth (or inhibition) of the pathogenic strains and documentation of the results.

Cultivation

Lactobacilli

Cultivation from the deep frozen culture stored at −80° C. in 2 ml MRS broth (37° C., 24 h, anaerobically).

Fractionated smear on MRS agar (37° C., 48 h, anaerobically).

Inoculation of a colony into 10 ml MRS broth (37° C., 18 h, anaerobically).

A parallel smear from this culture is applied to agar plates.

*Candida albicans* and *Candida glabrata*

Cultivation from the deep frozen culture stored at −80° C. in 2 ml MRS broth (37° C., 24 h, aerobically).

Fractionated smear on MRS agar (37° C., 48 h, aerobically).

Inoculation of a colony into 10 ml MRS broth (37° C., 18 h, aerobically).

5 µl broth from this culture is spotted.

*Candida crusei*

Cultivation from the deep frozen culture stored at −80° C. in 2 ml BHI broth (37° C., 24 h, aerobically).

Fractionated smear on BHI agar (37° C., 48 h, aerobically).

Inoculation of a colony into 10 ml BHI broth (37° C., 18 h, aerobically).

5 µl broth from this culture is spotted.

*Escherichia coli*

Cultivation from the deep frozen culture stored at −80° C. in 2 ml BHI broth (37° C., 24 h, aerobically).

Fractionated smear on BHI agar (37° C., 48 h, aerobically).

Inoculation of a colony into 10 ml BHI broth (37° C., 18 h, aerobically).

5 µl broth from this culture is spotted. *Gardnerella vaginalis*

Cultivation from the deep frozen culture stored at −80° C. in 2 ml BHI broth (37° C., 24 h, anaerobically).

5 µl broth from this culture is spotted.

TABLE 8

Growth media and incubation conditions

| Species | Agar | Incubation |
|---|---|---|
| *Candida albicans* | MRS | 37° C. 48 h, anaerobic |
| *Candida glabrata* | MRS | 37° C. 48 h, anaerobic |
| *Candida krusei* | MRS | 37° C. 48 h, Aerobic |
| *Escherichia coli* | BHI | 37° C. 48 h, anaerobic |
| *Gardnerella vaginalis* | MRS starch agar (pH 6.7) | 37° C. 48 h, anaerobic |

Results

The detailed results are depicted in FIG. 1. In summary:

All Lactobacilli strains and five competing strains demonstrated strong inhibition of *Gardnerella vaginalis*.

With all Lactobacilli the inhibition of *Escherichia coli* was either not very pronounced or no inhibition could be detected.

The tests for the inhibition of *Candida albicans* by Lactobacilli showed some large differences in the strengths of the inhibitory effects with different strains. It was mainly the *Lactobacillus rhamnosus* strains, which caused a very strong to complete inhibition of the growth of *Candida albicans*

The inhibition of *Candida glabrata* by Lactobacilli was considerably weaker than the inhibition produced with *Candida albicans*. Here the inhibitory effect was again most pronounced with *Lactobacillus rhamnosus*.

Considerable differences in the strength of the inhibition could also be established in the tests for the inhibition of *Candida krusei*. A very strong inhibition of *Candida krusei* strains was generally caused by most Lactobacilli and again the *Lactobacillus rhamnosus* strains tended to have a somewhat greater inhibitory effect than representatives of the other three species. In the tests for the inhibition of *Candida krusei* a change in the strength of the inhibition could be observed over the course of time. This was in contrast to the other tests. The strength of the inhibition for some strains showed considerable differences between after 48 hours and after 120 hours. In almost all cases the inhibitory effect was less pronounced at 120 hours than at 48 hours.

C. Mutual Antagonism of the Lactobacilli Isolates

Mutual negative interactions on growth using a spotting-coating method for most combinations of the 12 selected strains have been investigated.

Materials and Methods

Cultivation

Cultivation from the deep frozen culture stored at −80° C. in 2 ml MRS broth (37° C., 24 h, aerobically).

Fractionated smear on MRS agar (37° C., 48 h, aerobically).

Inoculation of a colony into 10 ml MRS broth (37° C., 18 h, aerobically).

Spotting 5 µl broth from this culture onto the agar plates or the transfer of 200 µl bacterial suspension into 4.5 ml soft agar.

Spotting-Coating Method

Spotting 10 µl of bacterial suspension for each of the 11 strains being compared onto MRS agar: incubation at 37° C., 24 h, aerobically.

Transfer of 200 µl of the bacterial suspension of the test strain (12 strains) to 4.5 ml soft agar. Coating of the agar plates spotted on the previous day is carried out using this soft agar bacterial suspension. Incubation at 37° C., 24 h, aerobically.

Evaluation and documentation of the mutual inhibition after 24 hours and 48 hours.

Results

The strength of the mutual inhibition was assessed visually on a scale between − (no inhibition) and +++ (very strong inhibition) as shown in the following Table 9.

TABLE 9

Mutual inhibition of the 12 Lactobacilli strains

| | | LBV 10 | LBV 61 | LBV 88 | LBV 62 | LBV 150 | LBV 162 | LBV 8 | LBV 110 | LBV 116 | LBV 69 | LBV 96 | LBV 136 |
|---|---|---|---|---|---|---|---|---|---|---|---|---|---|
| *L. crispatus* | LBV 10 | | ++ | + | − | −/+ | − | + | −/+ | −/+ | + | + | + |
| | LBV 61 | + | | + | − | − | + | − | − | −/+ | + | + | + |
| | LBV 88 | ++ | ++/+++ | | + | + | + | + | −/+ | −/+ | + | + | +/++ |
| *L.* | LBV 62 | + | ++ | + | | − | − | − | − | − | − | −/+ | −/+ |

TABLE 9-continued

Mutual inhibition of the 12 Lactobacilli strains

|  |  | LBV 10 | LBV 61 | LBV 88 | LBV 62 | LBV 150 | LBV 162 | LBV 8 | LBV 110 | LBV 116 | LBV 69 | LBV 96 | LBV 136 |
|---|---|---|---|---|---|---|---|---|---|---|---|---|---|
| gasseri | LBV 150 | +/++ | + | - | - |  | - | - | - | - | - | - | - |
|  | LBV 162 | ++ | ++ | +/++ | - | -/+ |  | + | - | -/+ | + | + | - |
| L. jensenii | LBV 8 | - | + | - | - | - | - |  | - | - | - | - | - |
|  | LBV 110 | +/++ | +/++ | + | - | - | - | - |  | - | -/+ | - | - |
|  | LBV 116 | + | ++ | + | -/+ | - | - | + | - |  | -/+ | + | - |
| L. rhamnosus | LBV 69 | +++ | +++ | +++ | + | ++ | ++ | +/++ | + | ++ |  | ++ | ++ |
|  | LBV 96 | +++ | +++ | +++ | + | + | ++ | + | -/+ | + | +/++ |  | +/++ |
|  | LBV 136 | +++ | +++ | +++ | + | ++ | ++ | ++ | + | +/++ | ++ | ++ |  |

LBV 10: DSM 23744; LBV 61: DSM 23745; LBV 88: DSM 22566; LBV 62: DSM 23751; LBV 150N: DSM22583; LBV 162: DSM 23751; LBV 8: DSM 23746; LBV 110: DSM 23747; LBV 116: DSM 22567; LBV 69: DSM 23748; LBV 96: DSM 22560; LBV 136: DSM 23749

Large differences were established in the inhibitory effects of the 12 strains against each other.

The three *Lactobacillus crispatus* strains demonstrated either no inhibitory effect or only a weak inhibitory effect on the strains of the other species. The strains themselves were however considerably inhibited by all of the other strains.

The *Lactobacillus jensenii* and *Lactobacillus gasseri* strains mainly inhibited the *Lactobacillus crispatus* strains while the inhibitory effect towards the other strains was rather weak.

The strongest inhibitory effect was established for the *Lactobacillus rhamnosus* strains. These very strongly inhibited the three *Lactobacillus crispatus* strains and strongly inhibited the representatives of *Lactobacillus jensenii* and *Lb gasseri*. Each strain also showed a strong inhibitory effect towards both of the other *Lactobacillus rhamnosus* strains.

Mutual interactions are minimal for the preferred combination of *Lactobacillus crispatus* (DSM 22566), *Lactobacillus rhamnosus* (DSM 22560), *Lactobacillus jensenii* (DSM 22567) and *Lactobacillus gasseri* (DSM 22583). Under the latter conditions, only the strain *Lactobacillus crispatus* DSM 22566 is strongly inhibited by *Lactobacillus rhamnosus* DSM 22560.

Example 3

Pilot Study with the Lactobacilli Composition [*Lactobacillus crispatus* (DSM 22566), *Lactobacillus rhamnosus* (DSM 22560), *Lactobacillus jensenii* (DSM 22567) and *Lactobacillus gasseri* (DSM 22583)] of the Invention In a unique pilot study the human Lactobacilli composition (cultivation out of human Lactobacilli) was tested in vivo. These human Lactobacilli were isolated out of a study with pregnant women. Lactobacilli in pregnancies play an important role to protect women from vaginal infections in order to protect the fetus maintaining a healthy flora in pregnancy. Vaginal infection in pregnancy is associated with preterm delivery, preterm labour and poor pregnancy outcome. To date data of a study with 9 women (neovagina, no communication with the abdominal cavity, no uterus) are available; Lactobacilli (Composition 1, Table 1) were orally administered, vaginal samples were taken before oral administration, then one week after oral daily intake and third vaginal samples after one week without probiotic treatment were taken to see a long term effect.

Figure 3:
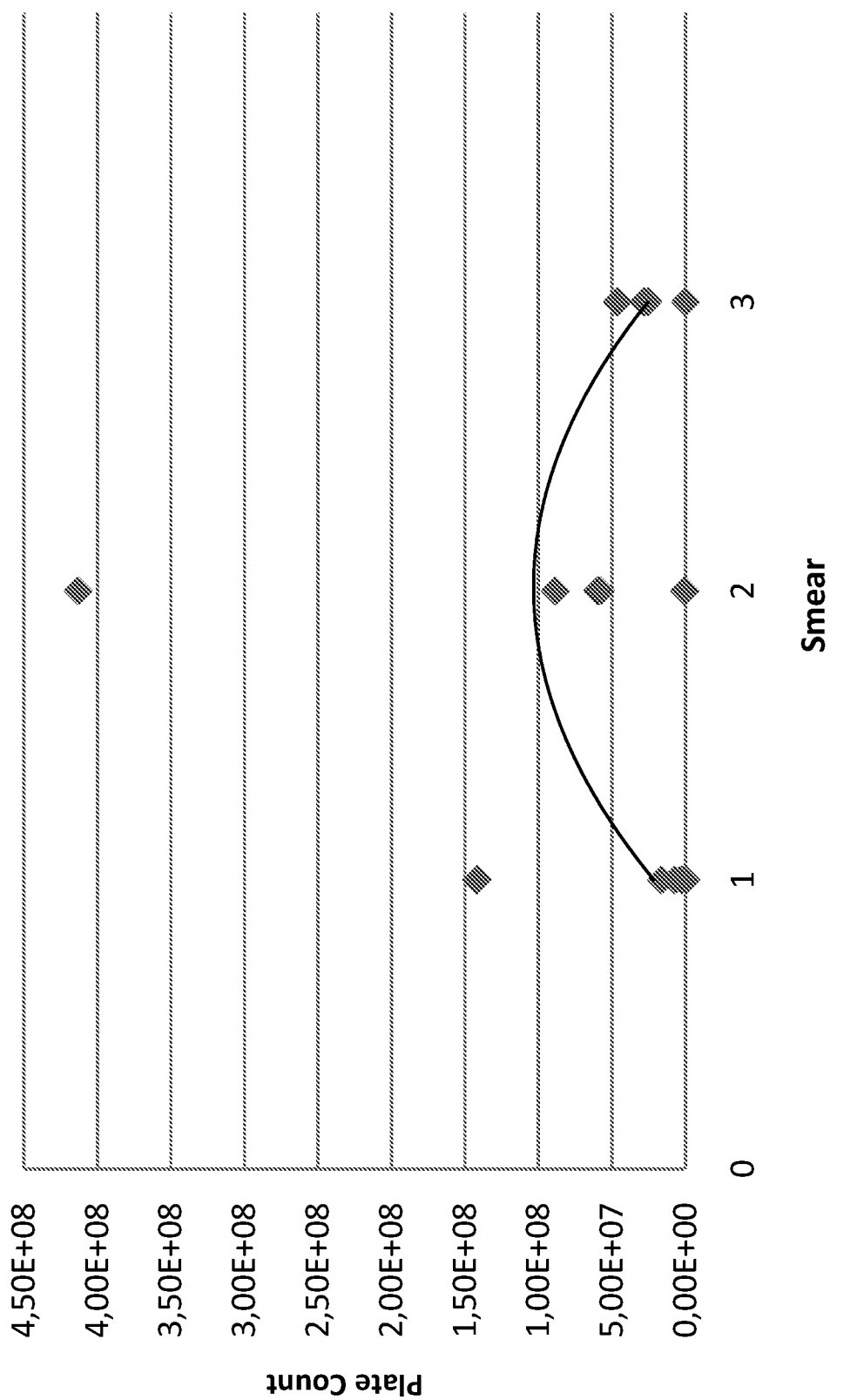

FIGS. 2 and 3 show the over all median concentration of Lactobacilli: at the beginning of study, the levels were low (median 3,07E+06; $SD^{+/-5,23}E+07$); after oral intake concentration increased (median 5,77E+07; SD 1,72E08); after a one week, dose-free interval, levels were higher than before therapy (median 2,71E+07).

Figure 4:
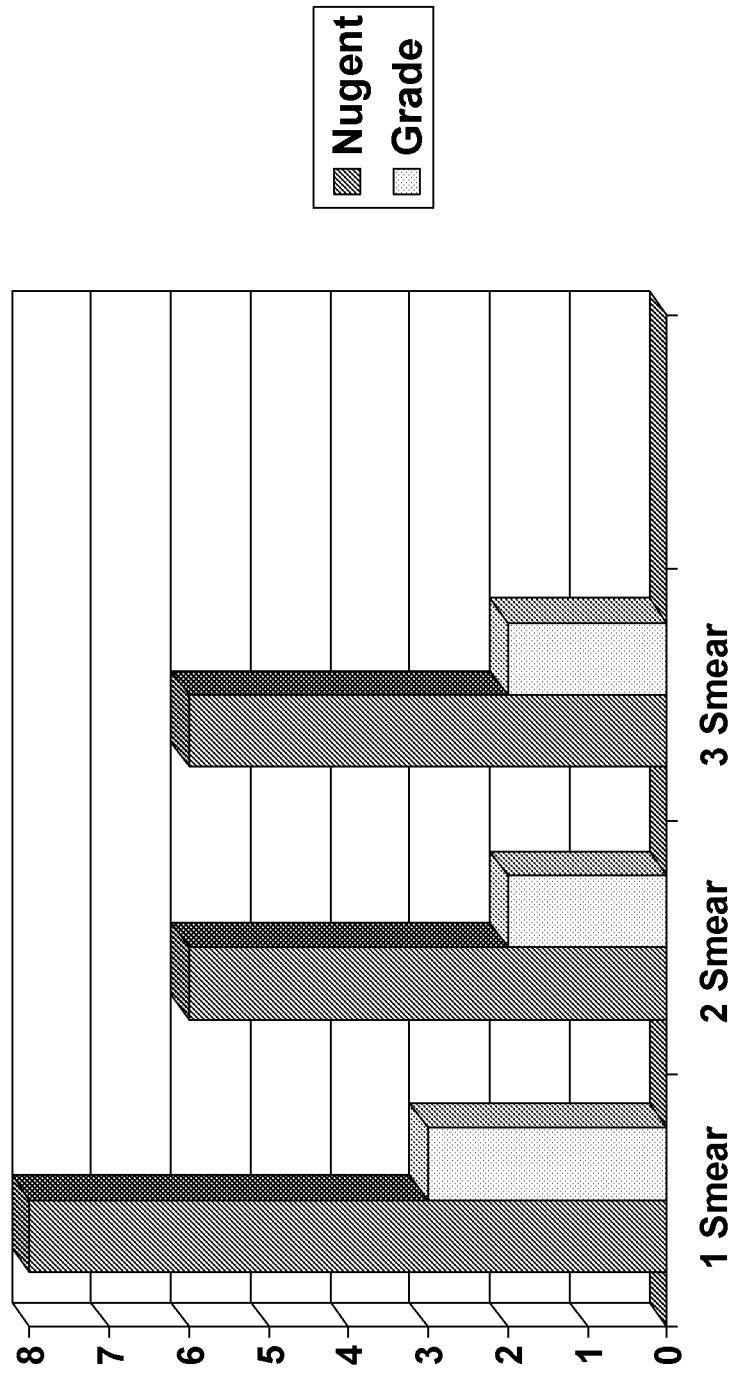
FIG. 4 shows the change in Nugent score and the change from bacterial vaginosis to an intermediate vaginal flora in the clinical study of Example 3.

FIG. 4 shows the change in Nugent score and the change from bacterial vaginosis (grade 3) to an intermediate vaginal flora (grade 2): Median Nugent score before probiotic administration was 8 (SD 1.07) which means a grade 3 of the vaginal flora (bacterial vaginosis in clinical terms). After one week, improvement of the Nugent scores to score 6 (SD 0.79) which means grade 2, intermediate flora, no more bacterial vaginosis. After one more week this clinical microbiological diagnosis was unchanged, Nugent score 6 (SD 1.79), grade 2 (SD 0.55).

Example 4

Interim-Analysis of an Ongoing Clinical Trial

The ability of the orally administered preparation of four probiotic *lactobacillus* strains according to the invention [*Lactobacillus crispatus* (DSM 22566), *Lactobacillus rhamnosus* (DSM 22560), *Lactobacillus jensenii* (DSM 22567) and *Lactobacillus gasseri* (DSM 22583)] to improve the quality of the flora of neovagina was investigated in a placebo-controlled, double-blind trial (n=70).

To date 31 women completed trial.

The protocol treatment was the following:

Initial swab (nugent and culture and PCR-Test on anaerobic bacteria). One week oral administration of the lactobacilli composition.

Second swab (nugent and culture and PCR-Test on anaerobic bacteria). One week without probiotics.

Third swab (nugent and culture and PCR-Test on anaerobic bacteria)

Figure 5:
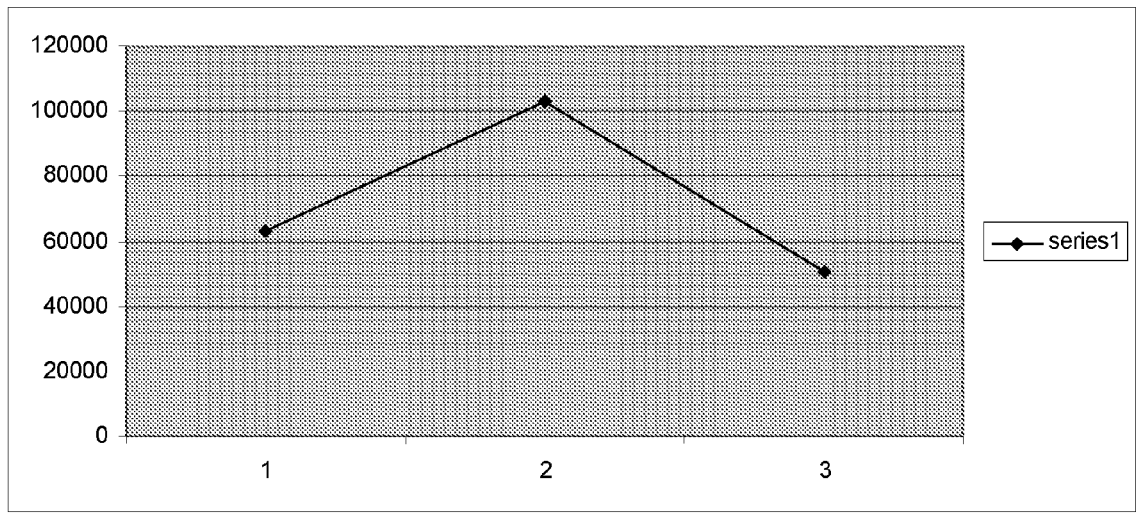
FIG. 5 shows the analysis of Lactobacilli concentration after oral administration of the Lactobacilli composition [*Lactobacillus crispatus* (DSM 22566), *Lactobacillus rhamnosus* (DSM 22560), *Lactobacillus jensenii* (DSM 22567) and *Lactobacillus gasseri* (DSM 22583)] in clinical trial.
Figure 6:
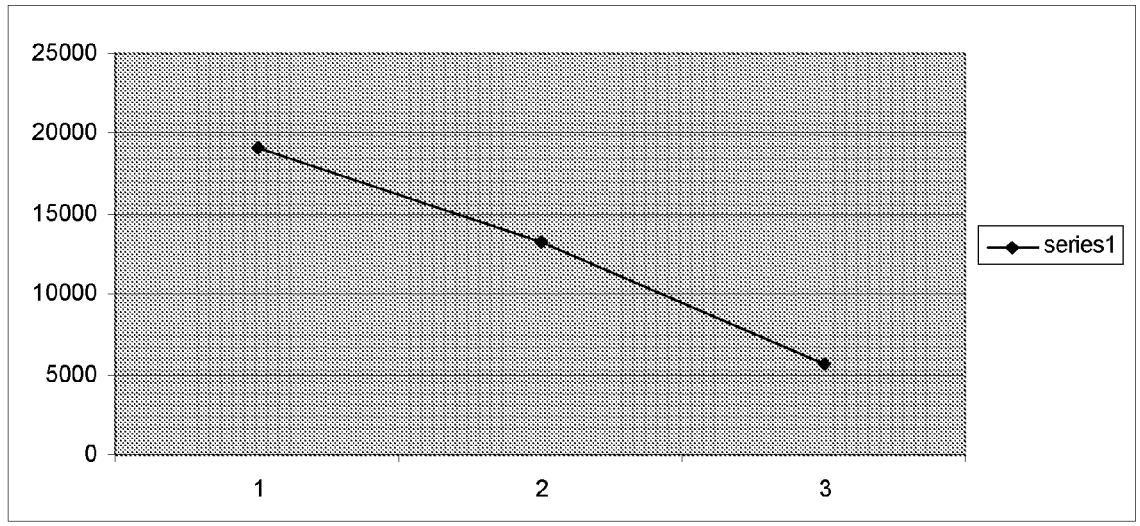
FIG. 6 shows the analysis of Lactobacilli concentration in a placebo group.

FIG. 5 shows the results in term of concentration of Lactobacilli in the vagina during the study (1: initial swab; 2: after oral intake; 3: observation). FIG. 6 shows the results of the parallel analysis carried out on the placebo group. First data show significant rise of *Lactobacillus* concentration after one week oral administration. No rise of Lactobacilli was observed in the placebo group.

Example 5

Comparison between the Lactobacilli strains of a Competitor Product (Ellen) and the Strains of the Invention Lactobacilli Strains Lactobacilli strains of the prior art:

*L. gasseri* (LN40, Tam1, Lb311)

*L. fermentum* (LN99, Tam2, Lb312)

*L. rhamnosus* (casei) (LN 113-2, Tam3, Lb 313) in the following named "Ellen" strains.

Lactobacilli strains of the invention:
 *L. rhamnosus* DSM22560 (LBV96, Lb322)
 *L. crispatus* DSM22566 (LBV88, Lb323)
 *L. jensenii* DSM22567 (LBV116, Lb324)
 *L. gasseri* DSM 22583 (LBV150N, Lb325)

Experimental Procedures

The following analysis were carried out on "Ellen" strains in comparison with the strains of the invention.
 a. Culture from cryoculture
 b. Assessment of growth in aerobic or anaerobic culture
 c. Ability to lower pH value (acidification potential)
 d. Stability toward acid (HCl solution—stability against gastric juice)
 e. Stability toward bile salts
 f. Formation of extracellular hydrogen peroxide ($H_2O_2$)

a. Culture from Cryoculture

All strains were successfully grown in MRS broth from cryocultures stored at −80° C. All cultures used for investigation were not more than 24 h old.

b. Assessment of Growth in Aerobic or Anaerobic Culture

Assessment of the intensity of growth in aerobic or anaerobic culture is an important criterion for the selection of strains. Assessment of growth was on the basis of fractionated smear cultures of the strains on MRS-agar plates, incubated 48 h at 37° C. under aerobic or anaerobic conditions. Colony diameters were optically evaluated (+++, ++, +). Agar plates were documented with the aid of digital photographs. Results on the basis of two analyses are shown in the following Table 10:

TABLE 10

| Aerob. | Anaerob. | |
|---|---|---|
| + | +++ | *L. gasseri* (LN40, Tam1, Lb311) |
| ++ | +++ | *L. fermentum* (LN99, Tam2, Lb312) |
| +++ | +++ | *L. rhamnosus* (LN 113-2, Tam3, Lb 313) |
| +++ | +++ | *L. rhamnosus* DSM22560 (LBV96, Lb322) |
| + | +++ | *L. crispatus* DSM22566 (LBV88, Lb323) |
| + | +++ | *L. jensenii* DSM22567 (LBV116, Lb324) |
| ++ | +++ | *L. gasseri* DSM 22583 (LBV150N, Lb325) |

Both *Lactobacillus rhamnosus* strains (ELLEN LN 113-2 and *L. rhamnosus* DSM22560) grow well. Under aerobic conditions, there is slightly better growth of the *L. gasseri* strain DSM 22583 versus the ELLEN *L. gasseri* strain LN 40.

c. pH-Lowering Capability (Acidification Activity)

The pH lowering capabilities of the seven strains were determined following incubation under anaerobic conditions for 48 h at 37° C. in 10 ml MRS-broth (starting pH=5.8). The pH-values resulting in the broths were determined in triplicate using a standard pH-meter. Resulting capability to lower pH (arithmetic mean of three measurements) are shown in the following Table 11.

TABLE 11

| pH 3.729 | *L. gasseri* (LN40, Tam1, Lb311) |
|---|---|
| pH 4.186 | *L. fermentum* (LN99, Tam2, Lb312) |
| pH 3.824 | *L. rhamnosus* (LN 113-2, Tam3, Lb 313) |
| pH 3.657 | *L. rhamnosus* DSM22560 (LBV96, Lb322) |
| pH 3.636 | *L. crispatus* DSM22566 (LBV88, Lb323) |
| pH 3.946 | *L. jensenii* DSM22567 (LBV116, Lb324) |
| pH 4.147 | *L. gasseri* DSM 22583 (LBV150N, Lb325) |

While the ELLEN strain *L. gasseri* LN 40 is capable of lowering the pH below the corresponding level achieved by *L. gasseri* DSM 22583 (pH=3.73 vs. pH 4.15), the *L. rhamnosus* strains showed an inverse result (LN 113-2: pH=3.82 vs. DSM 22560 pH=3.66). The most pronounced lowering of pH value is achieved by the *L. crispatus* strain DSM22566 (pH=3.64).

d. Stability Under Acid Stress (HCl Solution; Resistance Against Gastric Juice)

Stability under acid stress of 3 hours duration of the *Lactobacillus* strains was determined in duplicate in MRS broth adjusted to pH values of 2, 2.5, 3, 3.5 and 4 with 1 M hydrochloric acid. From a starter culture in MRS broth, 9.9 ml portions of the acidified broths were inoculated with 100 µl and incubated at 37° C. for 3 h under anaerobic conditions. The determination of the starting bacterial count (present in each inoculum) was performed in parallel using the plate count method (in duplicate, 37° C., 48 h, anaerobic conditions). Following hours incubation, the plate counts of the cultures incubated at different pH values were determined using a similar procedure. Stability was calculated in relation to the respective starting plate count. Results are shown in the following Table 12 as arithmetic mean of two independent investigations.

TABLE 12

| *L. gasseri* (LN40, Tam1, Lb311) starting plate count $4.5 \times 10^6$ | |
|---|---|
| pH 2.0 | $5.9 \times 10^4$ |
| pH 2.5 | $5.0 \times 10^5$ |
| pH 3.0 | $4.9 \times 10^6$ |
| pH 3.5 | $6.9 \times 10^6$ |
| pH 4.0 | $7.0 \times 10^6$ |
| *L. fermentum* (LN99, Tam2, Lb312) starting plate count $2.3 \times 10^5$ | |
| pH 2.0 | $9.6 \times 10^4$ |
| pH 2.5 | $3.5 \times 10^7$ |
| pH 3.0 | $4.3 \times 10^7$ |
| pH 3.5 | $3.2 \times 10^7$ |
| pH 4.0 | $4.0 \times 10^7$ |
| *L. rhamnosus* (LN 113-2, Tam3, Lb 313) starting plate count $3.0 \times 10^4$ | |
| pH 2.0 | $4.9 \times 10^3$ |
| pH 2.5 | $5.6 \times 10^3$ |
| pH 3.0 | $3.2 \times 10^5$ |
| pH 3.5 | $5.2 \times 10^5$ |
| pH 4.0 | $3.4 \times 10^5$ |
| *L. rhamnosus* DSM22560 (LBV96, Lb322) starting plate count $1.9 \times 10^5$ | |
| pH 2.0 | $2.5 \times 10^4$ |
| pH 2.5 | $8.6 \times 10^5$ |
| pH 3.0 | $1.5 \times 10^6$ |
| pH 3.5 | $2.1 \times 10^6$ |
| pH 4.0 | $3.9 \times 10^6$ |
| *L. crispatus* DSM22566 (LBV88, Lb323) starting plate count $1.1 \times 10^5$ | |
| pH 2.0 | $4.7 \times 10^4$ |
| pH 2.5 | $8.0 \times 10^4$ |
| pH 3.0 | $1.4 \times 10^7$ |
| pH 3.5 | $1.2 \times 10^7$ |
| pH 4.0 | $1.5 \times 10^7$ |
| *L. jensenii* DSM22567 (LBV116, Lb324) starting plate count $6.9 \times 10^5$ | |
| pH 2.0 | no growth |
| pH 2.5 | $1.1 \times 10^4$ |
| pH 3.0 | $6.4 \times 10^5$ |
| pH 3.5 | $4.1 \times 10^6$ |
| pH 4.0 | $1.1 \times 10^7$ |

TABLE 12-continued

| L. gasseri DSM 22583 (LBV150N, Lb325) starting plate count $1.1 \times 10^4$ | |
|---|---|
| pH 2.0 | $2.2 \times 10^6$ |
| pH 2.5 | $1.2 \times 10^6$ |
| pH 3.0 | $1.9 \times 10^6$ |
| pH 3.5 | $2.5 \times 10^6$ |
| pH 4.0 | $1.4 \times 10^6$ |

*L. gasseri* DSM 22583 showed the highest stability under acid stress. The plate count of this strain did not decrease but even increased at a pH value as low as 2.0. In contrast with ELLEN strain *L. rhamnosus* LN 113-2, *L. rhamnosus* DSM 22560 showed increasing plate counts at pH values of 2.5, 3.0, 3.5 and 4.0, showing decreased counts only at pH=2.

Lowering of pH is an important mechanism of action by which lactobacilli kill undesired microorganisms.

Concerning stability in gastric juice and growth under acidic conditions the Lactobacilli strains of the invention show clear advantages.

e. Stability Toward Bile Salts

Stability toward bile salts was investigated using fractional smears of the 7 strains on MRS agar plates with different concentrations of bile salts (0%; 0.1%; 0.2%; 0.3%; 0.4% and 0.5% (B8756-100G, Bile Salts, Sigma). Following anaerobic incubation at 37° C. for 48 h, the amount of growth was visually assessed: very good (+++), good (++), slight (+), no growth (−). The following Table 13 shows the results of stability toward bile salts (mean of duplicate determinations).

TABLE 13

| Bile salts conc. (%) | LN 40 | LN 99 | LN 113-2 | LBV 96 | LBV 88 | LBV 116 | LBV 150N |
|---|---|---|---|---|---|---|---|
| 0 | +++ | +++ | +++ | +++ | +++ | +++ | +++ |
| 0.1 | + | ++ | ++ | ++ | ++ | + | ++ |
| 0.2 | − | − | + | + | + | + | + |
| 0.3 | − | − | − | − | − | − | − |
| 0.4 | − | − | − | − | − | − | − |
| 0.5 | − | − | − | − | − | − | − |

All the strains of the invention showed better tolerance of bile salts (0.2%). Higher concentration of bile salts in the duodenum result in the death of many bacteria. The strains of the invention show clear advantages here, important especially for oral application.

f. Formation of Extracellular Hydrogen Peroxide.

Two methods for determination of $H_2O_2$ were selected and applied.

The 7 lactobacilli strains were examined for their ability to produce $H_2O_2$ using semi-quantitative $H_2O_2$ test strips (1.10081.0001, Merck). Following incubation in MRS broth at 37° C. for 48 h under anaerobic conditions, the cultures were shaken on a rotary shaker for 60 min under aerobic conditions. Table 14 shows the results of semi-quantitative determination of $H_2O_2$-production.

Agar medium for detection of $H_2O_2$: Addition of 0.25 mg/ml 3.3',5.5'-Tetramethyl-benzidine (TMB) (860336, Sigma) and 0.01 mg/ml horseradish peroxidase (P8375-2KU, Sigma) to MRS-Agar. The 7 lactobacilli strains were fractionally streaked onto the medium and incubated at 37° C. for 5 days under anaerobic conditions (Genbag Anaerob System, Biomerieux). Subsequently, the plates were exposed to atmospheric air, and the intensity of $H_2O_2$ formation assessed after 30 and 60 min (blue coloration upon exposure to oxygen due to $H_2O_2$ formed). Table 15 shows the results obtained by the agar method for determination of $H_2O_2$ production.

TABLE 14

| Time of measurement | LN 40 | LN 99 | LN 113-2 | LBV 96 | LBV 88 | LBV 116 | LBV 150N |
|---|---|---|---|---|---|---|---|
| 0 min | 0 | 0 | 0 | 0 | 0 | 0 | 0 |
| 60 min | 0 | 0 | 0 | 0 | 0 | 1 | 3 |

0 = no reaction; 1 = 1 mg mg/l $H_2O_2$; 3 = 3 mg mg/l $H_2O_2$

TABLE 15

| Time of evaluation | LN 40 | LN 99 | LN 113-2 | LBV 96 | LBV 88 | LBV 116 | LBV 150N |
|---|---|---|---|---|---|---|---|
| 30 min | − | − | − | − | + | ++ | ++ |
| 60 min | − | − | − | + | +++ | +++ | +++ |

While none of the ELLEN strains produced measurable hydrogen peroxide, the strain *L. rhamnosus* LBV 96 (DSM22560) showed slight production and the other strains of the invention showed significant production of extracellular hydrogen peroxide (see Tables 14 and 15). As hydrogen peroxide serves to kill noxious microorganisms, this is an important advantage for the composition of Lactobacilli strains of the invention.

BIBLIOGRAPHY

1. Erickson K L, Hubbard N E. Probiotic immunomodulation in health and disease. J. Nutr. 2000; 130(2S Suppl):403-409.
2. Reid G, Cook R L, Bruce A W. Examination of strains of lactobacilli for properties that may influence bacterial interference in the urinary tract. J. Urol. 1987 August; 138(2):330-5.
3. Goldenberg, R. L., J. C. Hauth, and W. W. Andrews. 2000. Intrauterine infection and preterm delivery. N. Engl. J. Med. 342:1500-1507.
4. Spiegel, C. A., R. Amsel, D. Eschenbach et al. 1980. Anaerobic bacteria in nonspecific vaginitis. N. Engl. J. Med. 303:601-607.
5. Spiegel, C. A. 1991. Bacterial vaginosis. Clin. Microbiol. Rev. 4:485-502.
6. Forsum, U., E. Holst, P. G. Larsson et al. 2005. Bacterial vaginosis—a microbiological and immunological enigma. APMIS. 113:81-90.
7. Nugent, R. P., M. A. Krohn, and S. L. Hillier. 1991. Reliability of diagnosing bacterial vaginosis is improved by a standardized method of gram stain interpretation. J. Clin. Microbiol. 29:297-301.
8. Korn, A., G. Bolan, N. Padian et al. 1995. Plasma cell endometritis in women with symptomatic bacterial vaginosis. Obstet. Gynecol. 85:387-390.
9. Ness, R., S. Hillier, K. Kip et al. 2004. Bacterial vaginosis and risk of pelvic inflammatory disease. Obstet. Gynecol. 104:761-769.
10. Pandit L, Ouslander J G. Postmenopausal vaginal atrophy and atrophic vaginitis. Am J Med. Sci. 1997; 314(4):228-31.
11. Ginkel P D, Soper D E, Bump R C, Dalton H P. The vaginal flora in postmenopausal women: the effect of estrogen replacement therapy. Infect Dis Obstet. Gynecol. 1993; 1 94-97.

12. Raz R, Stamm W E. A controlled trial of intravaginal estriol in postmenopausal women with recurrent urinary tract infection. N Eng J. Med. 1993; 329 (11):735-6.
13. Kandler, O., and N. Weiss. 1986. Genus *Lactobacillus*, pp. 1063-1065. In, P. H. A. Sneath, N. S. Mair, M. E. Sharpe, and J. G. Holt (eds.), Bergey's Manual of Systematic Bacteriology, vol 2, 9th ed. Williams and Wilkins, Baltimore.
14. Vasquez, A., T. Jakobsson, S. Ahrne, U. Frosum, and G. Molin. 2002. Vaginal *Lactobacillus* flora of healthy Swedish women. J. Clin. Microbiol. 40:2746-2749.
15. Reid, G., J. A. McGroarty, L. Tomeczek, and A. W. Bruce. 1996. Identification and plasmid profiles of *Lactobacillus* species from the vagina of 100 healthy women. FEMS Immunol. Med. Microbiol. 15:23-26.
16. H. Kiss, B. Kogler, L. Petricevic, I. Sauerzapf, S. Klayraung, K. Domig, H. Viernstein, W. Kneifel. Vaginal *Lactobacillus microbiota* of healthy women in the late first trimester of pregnancy BJOG 2007; 114: 1402-1407
17. Uehara S, Monden K, Nomoto K, Seno Y, Kariyama R, Kumon H. A pilot study evaluating the safety and effectiveness of *Lactobacillus* vaginal suppositories in patients with recurrent urinary tract infection. Int J Antimicrob Agents. 2006; 28 (1):30-4.
18. Reid G. Charbonneau D, Erb J, Kochanowski B, Beuerman D, Poehner R, Bruce A W. Oral use of *Lactobacillus rhamnosus* GR-1 and *L. fermentum* GR-14 significantly alters vaginal flora: randomized, placebo-controlled trial in 64 healthy women. FEMS Immunology and Medical Microbiology 2003; 35:131-134.
19. Morelli L, Zonenenschain D, Del Piano M, Cognein A. Utilization of the intestinal tract as a delivery system for urogenital probiotics. J. Clin. Gastroenterol. 2004; 38 (6): 107-10.
20. Petricevic L, Unger F M, Viernstein H, Kiss H. Placebo-controlled, double-blind trial of *Lactobacillus* orally administered to improve the vaginal flora of postmenopausal women. Eur J Obstet Gyn R B 2008; 141: 54-57
21. Anukam K, Osazuwa E, Ahonkhai I, Ngwu M, Osemene G, Bruce A W, Reid G. Augmentation of antimicrobial metronidazole therapy of bacterial vaginosis with oral probiotic *L. rhamnosus* GL-1 and *L. reuteri* RC-14: randomized, double blind, placebo controlled trial. Microbes and Infection, 2006, 8: 1450-54.
22. Martinez R C R, Francescini S A, Patta M C, Quintana S M, Gomes B C De Martinis E C P, Reid G. Improved cure of bacterial vaginosis with single dose of tinidazole (2 g), *Lactobacillus rhamnosus* GR-1, and *Lactobacillus reuteri* RC-14: a randomized, double-blind, placebo-controlled trial. Can J. Microbiol. 2009; 55(2):133-8.
23. JIN L., L. TAO, S. I. PAVLOVA, J-S. SO, N. KIWANUKA, Z. NAMUKWAYA and B. A. SABER-BEIN: Species diversity and relative abundance of vaginal lactic acid bacteria from women in Uganda and Korea. Journal of Applied Microbiology. 2007; 102, 1107-115.

The invention claimed is:

1. A dietetic or pharmaceutical composition, comprising a group of at least four autochthonous human *Lactobacillus* strains, wherein said strains are selected from the group consisting of *Lactobacillus crispatus* (DSM 22566), *Lactobacillus rhamnosus* (DSM 22560), *Lactobacillus jensenii* (DSM 22567), *Lactobacillus gasseri* (DSM 22583), *Lactobacillus crispatus* (DSM 23744), *Lactobacillus crispatus* (DSM 23745), *Lactobacillus jensenii* (DSM 23746) *Lactobacillus jensenii* (DSM 23747), *Lactobacillus rhamnosus* (DSM 23748), *Lactobacillus rhamnosus* (DSM 23749), *Lactobacillus gasseri* (DSM 23750), and *Lactobacillus gasseri* (DSM 23751), together with at least one component select from the group consisting of a pharmaceutically or nutritionally-acceptable adjuvant and an excipient.

2. The composition according to claim 1, wherein the group of the at least four *Lactobacillus* strains consists of *Lactobacillus crispatus* (DSM 22566), *Lactobacillus rhamnosus* (DSM 22560), *Lactobacillus jensenii* (DSM 22567), and *Lactobacillus gasseri* (DSM 22583).

3. The composition according to claim 1, wherein a concentration of each of the strains is from $0.05 \times 10^9$ CFU/g to $30 \times 10^9$ CFU/g.

4. The composition according to claim 2, wherein a concentration of the *Lactobacillus crispatus* (DSM 22566) is from $3 \times 10^9$ to $22 \times 10^9$ CFU/g, a concentration of the *Lactobacillus rhamnosus* (DSM 22560) is from $3 \times 10^9$ to $22 \times 10^9$ CFU/g, a concentration of the *Lactobacillus jensenii* (DSM 22567) is from $0.7 \times 10^9$ to $6 \times 10^9$ CFU/g, and a concentration of the *Lactobacillus gasseri* (DSM 22583) is from $1 \times 10^9$ to $8 \times 10^9$ CFU/g.

5. The composition according to claim 4, wherein in a concentration of the *Lactobacillus crispatus* (DSM 22566) is $6 \times 10^9$ CFU/g, a concentration of the *Lactobacillus rhamnosus* (DSM 22560) is $6 \times 10^9$ CFU/g, a concentration of the *Lactobacillus jensenii* (DSM 22567) is $1.2 \times 10^9$ CFU/g, in a concentration of the *Lactobacillus gasseri* (DSM 22583) is $1.8 \times 10^9$ CFU/g.

6. The composition according to claim 4, comprising the following composition:

| Composition 1 | Quantity (mg/dose) | Guaranteed viable cell count (CFU/dose) | Initial viable cell count (CFU/dose) |
| --- | --- | --- | --- |
| L. crispatus Lbv88 (DSM 22566) | 15 | $1 \times 10^9$ | $1.5 \times 10^9$ |
| L. rhamnosus LbV96 (DSM 22560) | 15 | $1 \times 10^9$ | $1.5 \times 10^9$ |
| L. jensenii LbV 116 (DSM 22567) | 20 | $0.2 \times 10^9$ | $0.3 \times 10^9$ |
| L. gasseri LbV 150N (DSM 22583) | 9 | $0.3 \times 10^9$ | $0.45 \times 10^9$ |
| Potato maltodextrin | 161 | | |
| Insoluble dietary fiber | 25 | | |
| Silicium dioxide | 5 | | |
| Total | 250 | | |

7. The composition according to claim 4, comprising the following composition:

| Composition 2 | Quantity (mg/dose) | Guaranteed viable cell count (CFU/dose) | Initial viable cell count (CFU/dose) |
| --- | --- | --- | --- |
| L. crispatus Lbv88 (DSM 22566) | 50 | $1 \times 10^9$ | $5 \times 10^9$ |
| L. rhamnosus LbV96 (DSM 22560) | 50 | $1 \times 10^9$ | $5 \times 10^9$ |
| L. jensenii LbV 116 (DSM 22567) | 67 | $0.2 \times 10^9$ | $1 \times 10^9$ |
| L. gasseri LbV 150N (DSM 22583) | 30 | $0.3 \times 10^9$ | $1.5 \times 10^9$ |
| Potato maltodextrin | 23 | | |
| Insoluble dietary fiber | 25 | | |
| Silicium dioxide | 5 | | |
| Total | 250 | | |

8. A method for remedying deficiency of *Lactobacillus flora* comprising administering orally or topically vaginal the pharmaceutical composition according to claim 1 to a subject in need thereof.

9. The method according to claim 8, wherein the composition of claim 1 is administered in the form of at least one selected from the group consisting of a suppository, a vaginal capsule for vaginal administration, a coated capsule, a tablet, a sachet, a pill, a pearl, a vial, and an orally-consumed composition.

10. A method for treatment of vaginal and female genital and urogenital infection and urinary tract infections caused by *Lactobacillus* deficiency, chronic bacterial vaginosis and chronic yeast infection, chronic urinary tract infection in menopause, and atrophic vaginitis or vaginosis, the method comprising administering the pharmaceutical composition according to claim 1 to a subject in need thereof.

11. A method for treatment of asymptomatic or recurrent bacterial vaginosis in pregnancy or preterm delivery caused by bacterial vaginosis, the method comprising administering the pharmaceutical composition according to claim 1 to a subject in need thereof.

12. A product, comprising a dietetic composition according to claim 1, wherein the product is at least one selected from the group consisting of an integrator, a dairy product, a nutrition drink and a nutrition feed.

13. A method for treatment of asymptomatic or recurrent bacterial vaginosis, preterm delivery caused by bacterial vaginosis, and vulvo-vaginal candidosis, the method comprising administering the dietetic composition according to claim 1, in the form of an integrator, a dairy product, a nutrition drink and a nutrition feed, to a subject in need thereof.

14. A method for treatment of affections of the urogenital tract of women, the method comprising administering the pharmaceutical composition according to claim 2 to a subject in need thereof.

15. The composition according to claim 1, which comprises microbial cultures.

16. The composition according to claim 1, which comprises lyophilized cultures or liquid cultures.

17. The composition according to claim 1, wherein a concentration of each of the strains is from $0.5 \times 10^9$ CFU/g to $25 \times 10^9$ CFU/g.

* * * * *